United States Patent
Matsuoka et al.

(10) Patent No.: US 11,977,045 B2
(45) Date of Patent: May 7, 2024

(54) HUMIDITY SENSOR DEVICE

(71) Applicant: Nippon Telegraph and Telephone Corporation, Tokyo (JP)

(72) Inventors: Hiroto Matsuoka, Tokyo (JP); Takako Ishihara, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 264 days.

(21) Appl. No.: 17/296,822

(22) PCT Filed: Nov. 12, 2019

(86) PCT No.: PCT/JP2019/044284
§ 371 (c)(1),
(2) Date: May 25, 2021

(87) PCT Pub. No.: WO2020/110701
PCT Pub. Date: Jun. 4, 2020

(65) Prior Publication Data
US 2022/0003708 A1    Jan. 6, 2022

(30) Foreign Application Priority Data

Nov. 27, 2018  (JP) .................................. 2018-220912

(51) Int. Cl.
*G01N 27/22*   (2006.01)
*A41D 1/00*    (2018.01)
*G01N 27/04*   (2006.01)

(52) U.S. Cl.
CPC ........... *G01N 27/223* (2013.01); *A41D 1/002* (2013.01); *G01N 27/048* (2013.01)

(58) Field of Classification Search
CPC .... G01N 27/048; G01N 25/56; G01N 27/223; A41D 1/002; A61B 5/6802
See application file for complete search history.

(56) References Cited

U.S. PATENT DOCUMENTS

| | | | |
|---|---|---|---|
| 4,643,351 A | 2/1987 | Fukamachi et al. | |
| 5,396,796 A * | 3/1995 | Kotani | G01N 27/121 73/431 |
| 10,485,475 B1 * | 11/2019 | Miller | A61B 5/1455 |

(Continued)

FOREIGN PATENT DOCUMENTS

| | | | | |
|---|---|---|---|---|
| CN | 106885608 A * | 6/2017 | ............ | G01D 21/02 |
| JP | S50113494 U | 2/1974 | | |

(Continued)

OTHER PUBLICATIONS

Iwai et al (JP 2017/070666 A)_Apr. 13, 2017_English translation with Figures (Year: 2017).*

(Continued)

*Primary Examiner* — Jermele M Hollington
*Assistant Examiner* — Suresh K Rajaputra
(74) *Attorney, Agent, or Firm* — Slater Matsil, LLP

(57) ABSTRACT

An embodiment humidity sensor device includes a humidity sensor including a measurement section for measuring humidity, a housing accommodating the humidity sensor while the measurement section is exposed to the outside, and a wall member protruding from a bottom surface of the housing and surrounding a periphery of the measurement section.

19 Claims, 3 Drawing Sheets

(56) References Cited

U.S. PATENT DOCUMENTS

| | | | |
|---|---|---|---|
| 2014/0076026 A1* | 3/2014 | Starling | G01N 27/00 |
| | | | 73/29.02 |
| 2016/0038083 A1* | 2/2016 | Ding | A61B 5/1135 |
| | | | 600/388 |
| 2017/0038325 A1* | 2/2017 | Takashima | G06K 19/0702 |
| 2018/0102039 A1* | 4/2018 | Furuland | A61B 5/6892 |
| 2019/0132948 A1* | 5/2019 | Longinotti-Buitoni et al. | |
| | | | A61B 5/6805 |
| 2019/0387823 A1* | 12/2019 | O'Brien | A41B 7/02 |

FOREIGN PATENT DOCUMENTS

| | | | | |
|---|---|---|---|---|
| JP | 61-26160 U | 2/1986 | | |
| JP | H0592706 U | 12/1993 | | |
| JP | 2005337896 A | 12/2005 | | |
| JP | 2017070666 A | * | 4/2017 | A61B 5/00 |
| JP | 2017070666 A | 4/2017 | | |

OTHER PUBLICATIONS

Bao (CN 106885608 A)_Jun. 23, 2017_English translation with Figures (Year: 2017).*
Teruko Tamura, "Science of Clothing Environment", Measurement of Clothing Mechanism, Kenpakusha, Dec. 10, 2004: p. 34, Fig. 50.

* cited by examiner

HUMIDITY SENSOR DEVICE

This patent application is a national phase filing under section 371 of PCT/JP2019/044284, filed Nov. 12, 2019, which claims the priority of Japanese patent application no. 2018-220912, filed Nov. 27, 2018, each of which is incorporated herein by reference in its entirety.

TECHNICAL FIELD

The present disclosure relates to a humidity sensor device and particularly to a humidity sensor device that measures humidity inside clothes.

BACKGROUND

In order to evaluate the comfort of clothes and prevent heat stroke, it is effective to accurately grasp the conditions of sweating and heat exchanging by accurately measuring the humidity inside clothes.

Hitherto, there is known a technique in which a probe of a humidity sensor is attached to the inside of clothes and is drawn out by wiring to measure the humidity inside the clothes with a logger (see Non Patent Literature 1). In the technique for measuring humidity inside the clothes disclosed in Non Patent Literature 1, a user needs to measure the humidity inside the clothes while carrying the logger.

Here, it is conceivable to measure humidity inside clothes by providing a measurement hole in clothes and attaching a humidity sensor device to the outside of the clothes so that a measurement surface of a humidity sensor is exposed from the hole.

CITATION LIST

Non Patent Literature

Non Patent Literature 1: Teruko Tamura, "Science of Clothing Environment", Measurement of Clothing Mechanism, Kenpakusha, Dec. 10, 2004: p. 34, FIG. 50.

SUMMARY

Technical Problem

However, if the clothes around the measurement hole are wet when measuring the humidity inside the clothes from the measurement hole by attaching the humidity sensor device of the related art to the outside of the clothes, water vapor generated in the cloth is mixed with air to be measured. As a result, it is difficult to accurately measure the humidity inside the clothes.

Embodiments of the present disclosure are contrived to solve the above-described problems and an object of the present disclosure is to provide a humidity sensor device capable of more accurately measuring humidity inside clothes even when the clothes are wet when the humidity sensor device is attached to the outside of the clothes.

Means for Solving the Problem

In order to solve the above-described problems, a humidity sensor device according to embodiments of the present disclosure includes a humidity sensor including a measurement section for measuring humidity, a main body configured to accommodate the humidity sensor while the measurement section is exposed to outside, and a wall member protruding from a surface of the main body and surrounding a periphery of the measurement section.

Further, in the humidity sensor device according to embodiments of the present disclosure, the wall member may be formed in contact with an outer periphery of the measurement section.

Further, in the humidity sensor device according to embodiments of the present disclosure, the measurement section may protrude from a surface of the main body and the wall member may protrude more than the measurement section.

Further, in the humidity sensor device according to embodiments of the present disclosure, the wall member may be integrally formed with the main body.

Further, in the humidity sensor device according to embodiments of the present disclosure, in a plan view, a shape of an outer periphery of the measurement section and a shape of an inner periphery of the wall member may be similar to each other.

Further, the humidity sensor device according to embodiments of the present disclosure may further include a control board configured to control an operation of the humidity sensor and output a value of humidity measured by the humidity sensor to outside, and a battery configured to supply power to the control board, in which the control board and the battery may be accommodated in the main body.

Further, the humidity sensor device according to embodiments of the present disclosure may further include clothes having a hole formed therein, in which the main body may be attached to the outside of the clothes, and the wall member may be inserted into the hole.

Effects of Embodiments of the Invention

According to embodiments of the present disclosure, because the wall member is provided to stand on the main body to surround the periphery of the measurement section of the humidity sensor, the wall member prevents contamination of water vapor generated in a cloth and hence humidity inside clothes can be more accurately measured.

DETAILED DESCRIPTION OF ILLUSTRATIVE EMBODIMENTS

Hereinafter, preferred embodiments of the present disclosure will be described in detail with reference to FIGS. 1 to 10.

A humidity sensor device 1 according to an embodiment is detachably attached to clothes worn by a user and measures the humidity inside the clothes.

Figure 1:
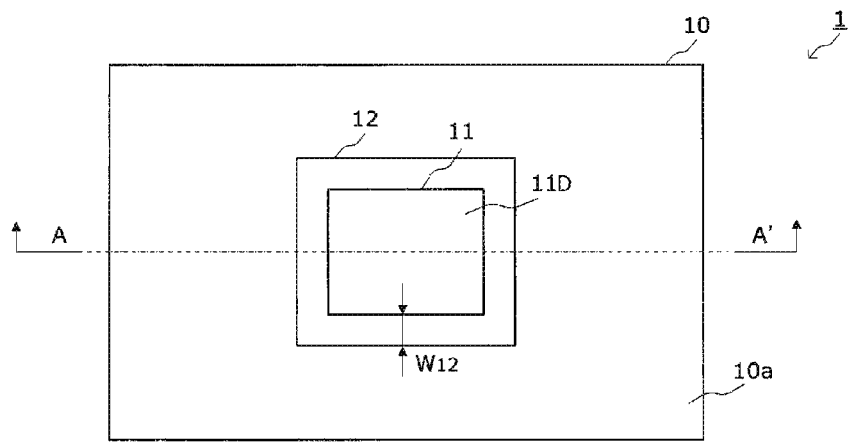
FIG. 1 is a bottom view of a humidity sensor device according to an embodiment of the present disclosure.
Figure 2:
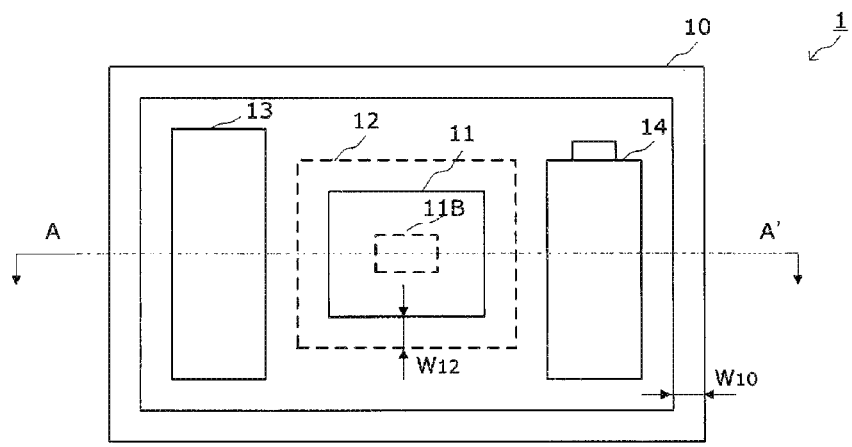
FIG. 2 is a plan view illustrating an internal structure of the humidity sensor device according to the embodiment.
Figure 3:
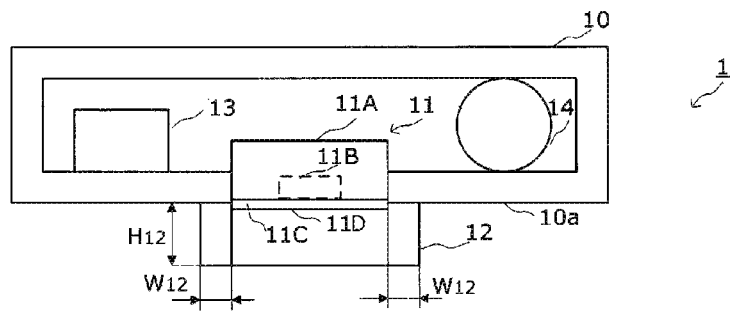
FIG. 3 is a cross-sectional view taken along a line A-A' of FIGS. 1 and 2.

The humidity sensor device 1 according to this embodiment includes, as illustrated in FIGS. 1 to 3, a housing 10 which is a main body, a humidity sensor 11 which is accommodated in the housing 10 and measures humidity, and a wall member 12 that is provided to stand on the housing 10. Further, a control board 13 and a battery 14 are accommodated inside the housing 10 in addition to the humidity sensor 11.

In this embodiment, the housing 10 is a container formed in a substantially rectangular parallelepiped shape. The housing 10 is formed of, for example, a polymer material such as ABS resin, rubber, or silicone resin. When a wall of the housing 10 is formed of a material having flexibility or elasticity such as rubber or silicone resin, it can be expected to improve the comfort of clothes to which the humidity sensor device 1 is attached as will be described later.

A thickness $W_{10}$ of the wall constituting the housing 10 can be set to, for example, about 1 mm, but is appropriately determined in consideration of the size and weight of the humidity sensor 11, the control board 13, and the battery 14 accommodated in the housing, the strength required from the planned usage environment of the humidity sensor device 1, and the like.

A hole is provided in a bottom surface 10a of the housing 10 and the humidity sensor 11 is fitted to the hole.

The humidity sensor 11 includes a sensor element 11B which outputs an electric signal in response to humidity of ambient air and a housing 11A which accommodates the sensor element 11B. As such a sensor element 11B, for example, a capacitance type or resistance type electric humidity sensor that measures a change in electrical characteristic of the moisture absorbent can be used. A high molecular polymer can be used as the moisture absorbent.

A window 11C is provided in a part of the housing 11A and the window 11C is covered with, for example, a member such as a metallic mesh through which ambient air can pass, so that a measurement section 11D is formed. The humidity sensor 11 converts the humidity of air introduced through the measurement section 11D or the window 11C into an electric signal by the sensor element 11B. In the example shown in FIG. 3, the measurement section 11D having a planar shape is exposed to the outside of the housing 10 while the humidity sensor 11 is fitted to the hole of the bottom surface 10a of the housing 10. Further, the measurement section 11D may protrude from the bottom surface 10a of the housing 10 to the outside.

The wall member 12 is formed in a cylindrical shape, protrudes from the outer surface of the bottom surface 10a of the housing 10, and surrounds the periphery of the measurement section 11D of the humidity sensor 11 exposed to the bottom surface 10a in a plan view. Further, the wall member 12 protrudes outward more than the measurement section 11D when the measurement section 11D of the humidity sensor 11 is exposed from the bottom surface 10a of the housing 10 and protrudes outward.

Preferably, as shown in FIGS. 1 and 2, the wall member 12 is formed in contact with the outer periphery of the measurement section 11D. The shape of the outer periphery of the wall member 12 is formed similarly to the shape of the measurement section 11D, for example, in a plan view, but the shape of the outer periphery of the wall member 12 is not limited thereto. For example, the shape of the outer periphery of the wall member 12 may be any shape different from the shape of the outer periphery of the humidity sensor 11, such as a circle, an ellipse, or a polygon. Additionally, the wall member 12 may not be formed in contact with a part or all of the outer periphery of the measurement section 11D.

The wall member 12 has, as shown in FIGS. 2 and 3, any thickness $W_{12}$ and a predetermined height $H_{12}$. The height $H_{12}$ of the wall member 12 can be set to, for example, about 3 mm to 5 mm. As the thickness $W_{12}$, for example, the same thickness as the thickness $W_{10}$ of the housing 10 may be used.

Such a wall member 12 is formed of a polymer material such as ABS resin, rubber, or silicone resin similarly to the housing 10. In this embodiment, the housing 10 and the wall member 12 are integrally formed with each other. However, the housing 10 and the wall member 12 may not be necessarily integrally formed with each other and both members may be fixed to each other by an adhesive after they are formed of the same or different materials.

Further, in this embodiment, the cylindrical wall member 12 is provided on the outer surface of the bottom surface 10a of the housing 10, but the wall member 12 may penetrate the hole formed in the bottom surface 10a of the housing 10 so that one end portion of the cylindrical wall member 12 is formed inside the housing 10.

The control board 13 controls the humidity sensor 11 and processes and outputs a signal indicating the humidity inside clothes measured by the humidity sensor 11. The control board 13 may include, for example, a communication circuit (not shown) and send out a measurement value to the outside by wireless communication including short-range wireless communication such as Bluetooth (trade name).

As the battery 14, for example, various batteries such as button type lithium batteries and lithium air batteries can be used. The battery 14 supplies power to the humidity sensor 11 and the control board 13.

Additionally, in this embodiment, an example in which the main body of the humidity sensor device 1 is formed by the hollow rectangular parallelepiped housing 10 has been described, but the main body can be formed by resin molding as long as the measurement section 11D of the humidity sensor 11 is exposed to the outside.

Further, the shape of the housing 10, that is, the main body is not limited to a rectangular parallelepiped shape and can be other shapes, for example, an elliptical or polygonal shape in a plan view in addition to a circular shape in a plan view such as a disk shape.

Next, an example in which the humidity sensor device 1 according to this embodiment is attached to clothes C will be described with reference to FIGS. 4 to 6.

Figure 4:
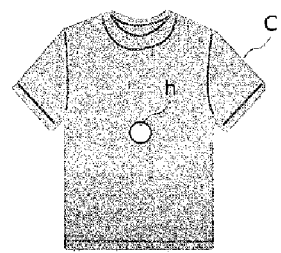
FIG. 4 is a diagram illustrating an example of clothes to which the humidity sensor device according to this embodiment is attached.

As illustrated in FIG. 4, for example, a circular measurement hole h is formed in the clothes C worn by a user. In addition, in the humidity sensor device 1 according to this embodiment, the shape of the hole h formed in the clothes C can be any shape if the size of the hole h is formed such that the wall member 12 can be inserted into the hole h.

Figure 5:
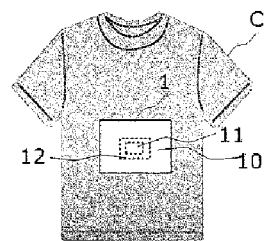
FIG. 5 is a diagram illustrating an example of clothes to which the humidity sensor device according to this embodiment is attached.

As shown in FIG. 5, the humidity sensor device 1 is attached to the outside of the clothes C. More specifically, the wall member 12 of the humidity sensor device 1 is inserted into the measurement hole h. Additionally, the bottom surface 10a of the humidity sensor device 1 may be detachably fixed to the outer cloth of the clothes C using, for example, a hook-and-loop fastener or the like.

Figure 6:
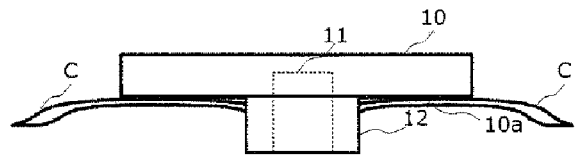
FIG. 6 is a side view illustrating a state in which the humidity sensor device according to this embodiment is attached to clothes.

As shown in FIG. 6, a region of the bottom surface 10a of the housing 10 other than the region of the wall member 12 and the measurement section 11D surrounded by the wall member 12 is in contact with the clothes C. In the example of FIG. 6, an end portion of the measurement hole h formed in the clothes C is in contact with the outer periphery of the wall member 12.

Here, a humidity sensor device 100 of an example of related art will be described with reference to FIGS. 8 to 10 for the comparison with the humidity sensor device 1 according to the embodiments.

Figure 8:
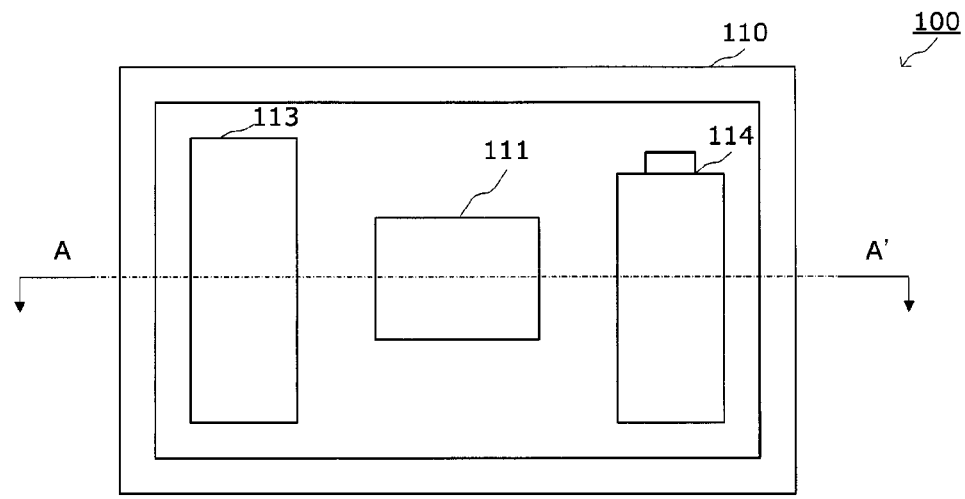
FIG. 8 is a plan view of a humidity sensor device according to an example of the related art.
Figure 9:
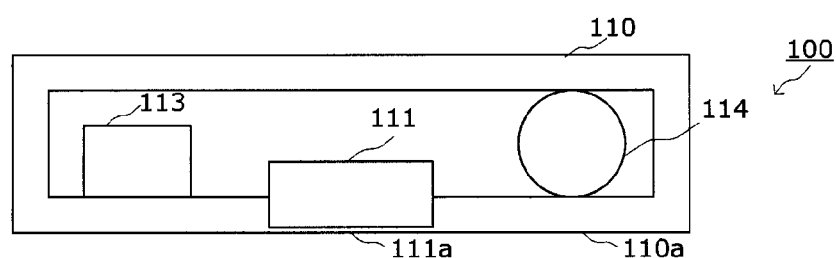
FIG. 9 is a cross-sectional view taken along a line A-A' of the humidity sensor device according to the example of the related art of FIG. 8.

The humidity sensor device 100 of the example of related art includes, as shown in FIG. 8, a housing 110, a humidity sensor 11, a control board 113, and a battery 114. The humidity sensor in is accommodated inside the housing 110. In the example of related art, the wall member 12 according to the embodiments of the present disclosure is not formed, and instead a concave portion is formed in a part of the region of the bottom surface 110a of the housing 110, and the humidity sensor in is disposed in the concave portion. As shown in FIG. 9, a measurement section 111a is formed in a region on the side of the bottom surface 110a of the humidity sensor in.

Figure 10:
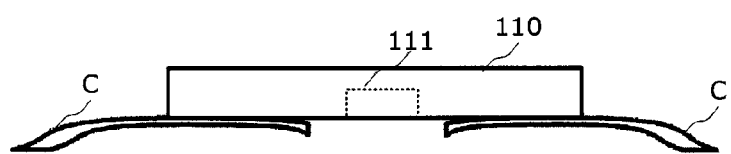
FIG. 10 is a side view of the humidity sensor device according to the example of the related art of FIG. 8.

Further, as shown in FIG. 10, according to a side view when the humidity sensor device 100 of the example of related art is attached to the clothes C, the clothes C are in contact with the bottom surface 110a of the housing 110 and any structure for blocking a space is not formed between the measurement section 111a and the end portion of the measurement hole.

Figure 7:
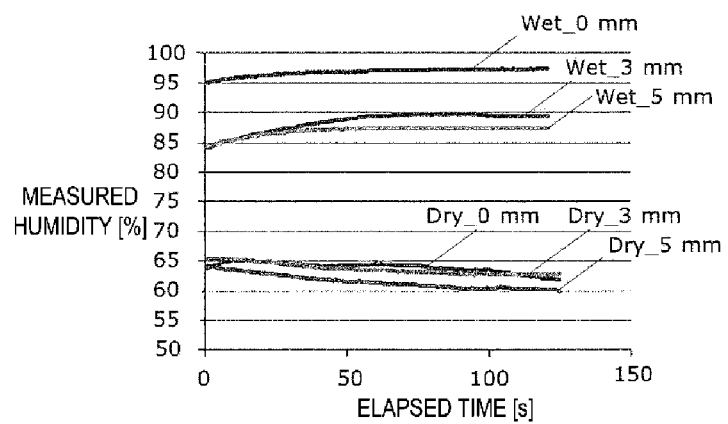
FIG. 7 is a diagram illustrating an effect of the humidity sensor device according to this embodiment.

Next, FIG. 7 shows a comparison with the humidity sensor device 100 of the example of related art regarding a relationship between measured humidity inside clothes and time using the height $H_{12}$ (o mm, 3 mm, 5 mm) of the wall member 12 of the humidity sensor device 1 according to an embodiment as a parameter. As shown in FIG. 7, a horizontal axis indicates an elapsed time (seconds) and a vertical axis indicates measured humidity (%) inside clothes. Further, FIG. 7 shows humidity inside clothes measured in each of the case in which the clothes C are wet (Wet) and the case in which the clothes C are not wet (Dry).

The value of humidity when the height $H_{12}$ of the wall member 12 is 0 mm is humidity inside clothes measured using the humidity sensor device 100 according to the example of related art. When the clothes C are not wet, the measured humidity values in the clothes of the example of related art (Dry_0 mm) and the humidity sensor device 1 (Dry_3 mm, Dry_5 mm) according to the embodiments are almost the same.

On the other hand, when the clothes C are wet, in the example of related art (Wet_0 mm), it can be seen that the measured humidity has risen to nearly 100% and is greatly affected by the vaporized water vapor in the clothes C. The humidity sensor device 1 according to the embodiments (Wet_3 mm, Wet_5 mm) also shows an increase in the value of measured humidity, but it can be seen that an increase in the value is suppressed by about 10% compared to the example of related art (Wet_0 mm).

Further, in the humidity sensor device 1 according to the embodiments, an increase in measured humidity inside the clothes is suppressed when the height $H_{12}$ of the wall member 12 is 5 mm compared to the case where the height is 3 mm. Thus, it can be said that an effect of suppressing an influence of water vapor evaporating in the cloth of the clothes C becomes higher as the height $H_{12}$ of the wall member 12 becomes higher.

As described above, the humidity sensor device 1 according to the embodiments includes the wall member 12 that protrudes from the bottom surface 10a of the housing 10 accommodating the humidity sensor 11 and surrounds the periphery of the measurement section 11D of the humidity sensor 11. Thus, even when the humidity sensor device 1 is attached to the outside of the clothes C, contamination of water vapor generated in a cloth is prevented and humidity inside clothes can be more accurately measured.

Further, in the humidity sensor device 1 according to the embodiments, the wall member 12 surrounding the measurement section 11D of the humidity sensor 11 is formed to protrude from the bottom surface 10a of the housing 10 toward the outside. Thus, even when the measurement section 11D of the humidity sensor 11 is provided to be exposed from the bottom surface 10a of the housing 10, the humidity inside clothes can be measured without contacting the clothes or the user's body.

Although the humidity sensor device of the embodiments of the present disclosure has been described above, the present disclosure is not limited to the above-described embodiments and can be modified into various forms that can be conceived by a person skilled in the art within the scope of the disclosure described in the embodiments.

REFERENCE SIGNS LIST

1 Humidity sensor device
10 Housing
10a Bottom surface
11 Humidity sensor
11A Housing
11B Sensor element
11C Window
11D Measurement section
12 Wall member
13 Control board
14 Battery
C Clothes
h Hole

The invention claimed is:

1. A humidity sensor device comprising:
   a humidity sensor configured to measure humidity while the humidity sensor is attached to an article of clothing, the humidity sensor including a measurement section;
   a main body separate from the article of clothing and configured to accommodate the humidity sensor while the measurement section is exposed to outside; and
   a wall member protruding vertically from a surface of the main body by a first predetermined height and surrounding a periphery of the measurement section, wherein the wall member defines a physical barrier between the humidity sensor and the article of clothing while the humidity sensor is attached to the article of clothing, and wherein the wall member and the main body are each made of a different type of material than the article of clothing.

2. The humidity sensor device according to claim 1, wherein the wall member is in contact with an outer periphery of the measurement section.

3. The humidity sensor device according to claim 1, wherein:
   the measurement section protrudes vertically from the surface of the main body by a second predetermined height, the second predetermined height being smaller than the first predetermined height.

4. The humidity sensor device according to claim 1, wherein the wall member is integrally formed with the main body.

5. The humidity sensor device according to claim 1, wherein in a plan view, a shape of an outer periphery of the measurement section and a shape of an inner periphery of the wall member are the same.

6. The humidity sensor device according to claim 1, further comprising:
   a control board configured to control an operation of the humidity sensor and output a value of humidity measured by the humidity sensor; and
   a battery configured to supply power to the control board, wherein the control board and the battery are accommodated in the main body.

7. The humidity sensor device according to claim 1, further comprising the article of clothing having a hole formed therein, wherein the main body is attached to an outside of the article of clothing and the wall member is inserted into the hole and provides a moisture barrier between the article of clothing and the measurement section.

8. The humidity sensor device according to claim 1, wherein the material of the article of clothing has a moisture-absorbing quality, and wherein the material of each of the wall member and the main body comprises ABS resin, rubber, or silicone resin.

9. The humidity sensor device according to claim 1, wherein the first predetermined height of the wall member is about 3 mm to about 5 mm.

10. A humidity sensor device comprising:
    a humidity sensor configured to measure humidity of ambient air behind an article of clothing while the humidity sensor is attached to the article of clothing, the humidity sensor including a sensor housing, a sensor element, a window, and a measurement section;
    a main body separate from the article of clothing and configured to accommodate the humidity sensor while the measurement section is exposed to outside;
    a wall member protruding vertically from a surface of the main body by a first predetermined height and surrounding a periphery of the measurement section, wherein the wall member defines a physical barrier between the humidity sensor and the article of clothing while the humidity sensor is attached to the article of clothing, and wherein the wall member and the main body are each made of a different type of material than the article of clothing;
    a control board accommodated in the main body and configured to control an operation of the humidity sensor and output a value of humidity measured by the humidity sensor; and
    a battery accommodated in the main body and configured to supply power to the control board and the humidity sensor.

11. The humidity sensor device according to claim 10, wherein the wall member is in contact with an outer periphery of the measurement section.

12. The humidity sensor device according to claim 10, wherein:
    the measurement section protrudes vertically from the surface of the main body by a second predetermined height, the second predetermined height being smaller than the first predetermined height.

13. The humidity sensor device according to claim 10, wherein the wall member is integrally formed with the main body.

14. The humidity sensor device according to claim 10, wherein in a plan view, a shape of an outer periphery of the measurement section and a shape of an inner periphery of the wall member are the same.

15. The humidity sensor device according to claim 10, wherein:
    the article of clothing includes a hole formed therein;
    the main body is attached to an outer surface of the article of clothing; and
    the wall member is inserted into the hole and provides a moisture barrier between the article of clothing and the measurement section.

16. The humidity sensor device according to claim 10, wherein the sensor element is configured to output an electric signal in response to the humidity of the ambient air.

17. The humidity sensor device according to claim 16, wherein the window is covered with a metallic mesh through which the ambient air can pass to the sensor element.

18. The humidity sensor device according to claim 10, wherein the material of the article of clothing has a moisture-absorbing quality, and wherein the material of each of the wall member and the main body comprises ABS resin, rubber, or silicone resin.

19. The humidity sensor device according to claim 10, wherein the first predetermined height of the wall member is about 3 mm to about 5 mm.

* * * * *